United States Patent
Richardson et al.

(10) Patent No.: US 9,983,172 B2
(45) Date of Patent: May 29, 2018

(54) MASS DETERMINATION USING ION MOBILITY MEASUREMENTS

(71) Applicant: Micromass UK Limited, Wilmslow (GB)

(72) Inventors: Keith George Richardson, High Peak (GB); John Brian Hoyes, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 23 days.

(21) Appl. No.: 15/098,927

(22) Filed: Apr. 14, 2016

(65) Prior Publication Data

US 2016/0305908 A1    Oct. 20, 2016

(30) Foreign Application Priority Data

Apr. 14, 2015  (GB) .................................. 1506330.8

(51) Int. Cl.
| | | |
|---|---|---|
| *G01N 27/62* | (2006.01) | |
| *H01J 49/42* | (2006.01) | |
| *H01J 49/00* | (2006.01) | |

(52) U.S. Cl.
CPC .......... *G01N 27/622* (2013.01); *H01J 49/004* (2013.01)

(58) Field of Classification Search
USPC ........ 250/281–283, 286, 287, 288, 292, 309
See application file for complete search history.

(56) References Cited

U.S. PATENT DOCUMENTS

| | | | | |
|---|---|---|---|---|
| 6,323,482 B1 * | 11/2001 | Clemmer | ............. | G01N 27/622 250/282 |
| 6,781,116 B2 | 8/2004 | Bateman | | |
| 6,960,761 B2 * | 11/2005 | Clemmer | ............. | G01N 27/622 250/287 |
| 7,576,321 B2 * | 8/2009 | Wu | ...................... | G01N 27/622 250/281 |
| 8,492,708 B2 * | 7/2013 | Wu | ...................... | G01N 27/622 250/281 |
| 9,607,817 B1 * | 3/2017 | Ugarov | ................... | H01J 49/04 |

(Continued)

FOREIGN PATENT DOCUMENTS

| | | |
|---|---|---|
| WO | 2011/017409 | 2/2011 |
| WO | 2011017409 | 2/2011 |

OTHER PUBLICATIONS

Matz L M et al., "Investigation of Drift Gas Selectivity in High Resolution Ion Mobility Spectrometry with Mass Spectrometry Detection", Journal of the American Society for Mass Spectrometry, Elsevier Science Inc., US, vol. 13, No. 4, pp. 300-307, Jan. 2002.

(Continued)

*Primary Examiner* — Bernard Souw

(57) ABSTRACT

A method of mass spectrometry is disclosed comprising: providing an algorithm or relationship that relates the ion mobilities of an analyte ion through three gases of different polarizability to the mass of the analyte ion; measuring the ion mobilities of an analyte ion through first, second and third different drift gases; and using the measured ion mobilities and said algorithm or relationship to determine the mass of the analyte ion. Embodiments of the invention enable the mass of an analyte to be determined without having to know the specific properties of the analyte ion.

18 Claims, 1 Drawing Sheet

(56) References Cited

U.S. PATENT DOCUMENTS

| | | | | |
|---|---|---|---|---|
| 2002/0014586 A1* | 2/2002 | Clemmer | ............. | G01N 27/622 |
| | | | | 250/287 |
| 2004/0094702 A1* | 5/2004 | Clemmer | ............. | G01N 27/622 |
| | | | | 250/283 |
| 2010/0224770 A1* | 9/2010 | Burns | ................... | G01N 27/622 |
| | | | | 250/252.1 |
| 2012/0228491 A1 | 9/2012 | Wu et al. | | |
| 2016/0084799 A1* | 3/2016 | Makarov | ............. | G01N 27/622 |
| | | | | 250/283 |
| 2016/0349212 A1* | 12/2016 | Bleiholder | ........... | G01N 27/622 |
| 2017/0076927 A1* | 3/2017 | Green | ................... | G01N 27/622 |
| 2017/0076928 A1* | 3/2017 | Ugarov | ............... | H01J 49/0031 |

OTHER PUBLICATIONS

G. W. Griffin et al., "Ion Mass Assignments Based on Mobility Measurements. Validity of Plasma Chromatographic Mass Mobility Correlations", Analytical Chemistry, vol. 45, No. 7, pp. 1204-1209, Jun. 1973.

Beegle L W et al., "Effects of drift-gas polarizability on glycine peptides in ion mobility spectrometry", International Journal of Mass Spectrometry, Elsevier Science Publishers, Amsterdam, NL, vol. 216, No. 3, pp. 257-268, May 2002.

Reid Asbury G et al., "Using Different Drift Gases to Change Separation Factors (alpha) in Ion Mobility Spectrometry", Analytical Chemistry, American Chemical Society, vol. 72, No. 3, pp. 580-584, Feb. 2000.

Mason et al., "Transport Properties of Ions in Gases", A Wiley-Interscience Publication, 1988.

* cited by examiner

MASS DETERMINATION USING ION MOBILITY MEASUREMENTS

CROSS-REFERENCE TO RELATED APPLICATION

This application claims priority from and the benefit of United Kingdom patent application No. 1506330.8 filed on 14 Apr. 2015, the entire contents of which are incorporated herein by reference.

FIELD OF THE INVENTION

The present invention relates generally to mass spectrometers and in particular to a mass spectrometer that may be operated at higher pressures.

BACKGROUND

Despite the widespread adoption of mass spectrometry across industry, healthcare and research, one of the barriers to further uptake of the technique is the cost, size and noise associated with the pumping that is needed to produce the required vacuum in the mass spectrometer.

It is therefore desired to provide an improved provide an improved method of mass spectrometry and an improved mass spectrometer.

SUMMARY

From a first aspect the present invention provides a method of mass spectrometry comprising:

providing an algorithm or relationship that relates the ion mobilities of an analyte ion through three gases of different polarizability to the mass of the analyte ion;

measuring the ion mobilities of an analyte ion through first, second and third different drift gases; and using the measured ion mobilities and said algorithm or relationship to determine the mass of the analyte ion.

The present invention recognises that by determining the ion mobilities of the same analyte ion in three different drift gases, the mass of the analyte can be determined without having to know the specific properties of the analyte ion (such as ion radius or properties related to analyte structure and charge distribution). This method of mass spectrometry is based on ion mobility spectrometry and so can be performed at relatively high pressures, eliminating the requirement for expensive and bulky vacuum pumps.

It will be appreciated that the term 'analyte ion' may relate to an ion population containing or consisting of a single type of analyte ion (i.e. a single molecular species) or may relate to an ion population containing or consisting of multiple isomers.

The only variables in the algorithm or relationship other than said mass may be variables representative of the ion mobilities of the analyte ion through the three different drift gases; or the only variables in the algorithm or relationship other than said mass may be variables representative of the ion mobilities of the analyte ion through the three different drift gases and physicochemical properties of the three different drift gases; and the method may comprise using the measured ion mobilities, said physicochemical properties of the first, second and third drift gases, and said algorithm or relationship to determine the mass of the analyte ion.

The method may comprise measuring the ion mobilities through said three gases of at least four different mass standard ions of known mass, and using these measured ion mobilities and known masses to derive said algorithm or relationship.

The step of measuring the ion mobilities may comprise measuring the ion mobilities of the same type of analyte ion through three different drift gases (a, b, c); and said relationship may be the following first equation:

$$P_{ab}R_{bc} - P_{bc}R_{ab} + P_{ab}g_c^{1/2}\mu_c^{-1/4} + P_{bc}g_a^{1/2}\mu_a^{-1/4} + P_{ca}g_b^{1/2}2\mu_b^{-1/4} = 0$$

wherein for any pair 'i' and 'j' of said drift gases, $P_{ij}$ is the polarizability of drift gas 'i' minus the polarizability of drift gas 'j'; wherein for any pair 'i' and 'j' of said drift gases, $R_{ij}$ is the radius of a drift gas molecule or atom for drift gas 'i' minus the radius of a drift gas molecule or atom for drift gas j; wherein for any given one of the drift gases n, the quantity $$g_n = \frac{3q}{16N_nK_n}\sqrt{\frac{2}{\pi kT_n}},$$

where q is the charge of the analyte ion, $N_n$ is the number density of the drift gas n, $K_n$ is the ion mobility of the analyte ion through drift gas n, k is the Boltzmann constant, and $T_n$ is the temperature of drift gas n; and wherein for any given one of the drift gases n, the reduced mass $$\mu_n = \frac{M_n m}{M_n + m},$$

where $M_n$ is the mass of a drift gas molecule or atom for drift gas n, and m is the required mass of the analyte ion.

From a second aspect, the present invention also provides a method of mass spectrometry comprising:

measuring the ion mobilities of the same type of analyte ion through three different drift gases (a, b, c); and using the measured ion mobilities to determine the mass of the analyte ion from the following first equation:

$$P_{ab}R_{bc} - P_{bc}R_{ab} + P_{ab}g_c^{1/2}\mu_c^{-1/4} + P_{bc}g_a^{1/2}\mu_a^{-1/4} + P_{ca}g_b^{1/2}2\mu_b^{-1/4} = 0$$

wherein for any pair 'i' and 'j' of said drift gases, $P_{ij}$ is the polarizability of drift gas 'i' minus the polarizability of drift gas 'j';

wherein for any pair 'i' and 'j' of said drift gases, $R_{ij}$ is the radius of a drift gas molecule or atom for drift gas 'i' minus the radius of a drift gas molecule or atom for drift gas j;

wherein for any given one of the drift gases n, the quantity $$g_n = \frac{3q}{16N_nK_n}\sqrt{\frac{2}{\pi kT_n}},$$

where q is the charge of the analyte ion, $N_n$ is the number density of the drift gas n, $K_n$ is the ion mobility of the analyte ion through drift gas n, k is the Boltzmann constant, and $T_n$ is the temperature of drift gas n; and wherein for any given one of the drift gases n, the reduced mass $$\mu_n = \frac{M_n m}{M_n + m},$$

where $M_n$ is the mass of a drift gas molecule or atom for drift gas n, and m is the required mass of the analyte ion.

The method may comprise determining the mass of the analyte ion by introducing the measured values of the ion mobilities ($K_n$) into the first equation; introducing known values, or measuring and introducing values, of $P_{ij}$, $R_{ij}$, q, $N_n$, $T_n$ and $M_n$ into the first equation; and solving the first equation for the mass of the analyte ion.

The polarizability of one, two or three of the three different drift gases may be known or may be measured according to the present invention.

The three gases have different polarizabilities.

The effective radius of the drift gas molecule or atom for each of the three different drift gases may be known or may be measured according to embodiments of the present invention.

The charge q of the analyte ion may be known or may be measured according to embodiments of the present invention. Alternatively, the value of q may be assumed to have a fixed value (e.g. one), or masses may be provided for a range of possible charge states.

The number density $N_n$ of one, two or three of the drift gases may be known or may be measured according to embodiments of the present invention.

The temperature $T_n$ of one, two or three of the drift gases may be known or may be measured according to embodiments of the present invention.

The mass of said drift gas molecule or atom for one, two or three of the drift gases may be known or may be measured according to embodiments of the present invention.

The at least one of said drift gases may be a substantially pure gas, rather than a composition of different gases.

The analyte ion may be an unknown analyte ion.

One, two or three of said drift gases may be maintained substantially at atmospheric pressure; or one, two or three of said drift gases may be maintained at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) >100 mbar; (viii) >1000 mbar; (ix) 0.0001-0.001 mbar; (x) 0.001-0.01 mbar; (xi) 0.01-0.1 mbar; (xii) 0.1-1 mbar; (xiii) 1-10 mbar; (xiv) 10-100 mbar; and (xv) 100-1000 mbar.

The step of measuring the ion mobilities of the analyte ion through the different drift gases may comprise measuring the drift time of the analyte ion through each of the three different drift gases.

The ion mobility through any one of the gases may be determined as the length of drift gas that the ion is urged through, divided by the product of the drift time along said length and the electric field strength of the electric field maintained along said length.

Alternatively, the ion mobility through any one of the gases may be determined by making measurements of drift time at several voltages and measuring the gradient of a best fit straight line relating inverse voltage to drift time.

The analyte ion may be an ion of a peptide or drug.

The relationship or first equation may be derived by, or said method may comprise deriving said relationship or first equation by:

(a) providing an equation for the ion mobility $K_n$ of the analyte ion through each of the three different gases, the equation being of the form:

$$K_n = \frac{3q}{16 N_n \Omega_n} \sqrt{\frac{2\pi}{\mu_n k T_n}},$$

where $\Omega_n$ is the collisional cross-section of the analyte ion in a given drift gas (n);

(b) providing an equation for the collisional cross-section of the analyte ion in each of the three different gases, the equation being of the form: $\Omega_n = \pi(R_n + r + \Phi P_n)^2$, where $R_n$ is the radius of a drift gas molecule or atom in a given drift gas (n), r is the radius of the analyte ion, φ is the polarizability coefficient, and $P_n$ is the polarizability of a given drift gas (n);

(c) substituting the term for the collisional cross-section from step (b) for each of the three different drift gases into its corresponding ion mobility equation from step (a), thereby providing three simultaneous equations for the three different gases in which the variable $\Omega_n$ is eliminated; and (d) solving or combining the three simultaneous equations so as to eliminate φ and r, and so as to provide said first equation.

Each of the drift gases may exhibit the relationship $\Omega_n = \pi(R_n + r + \Phi P_n)^2$, where $R_n$ is the radius of a drift gas molecule or atom in a given drift gas (n), r is the radius of the analyte ion, φ is the polarizability coefficient, and $P_n$ is the polarizability of a given drift gas (n).

The method may comprise empirically testing at least one of the drift gases using an analyte ion of known mass to determine if the at least one gas exhibits said relationship.

The three different drift gases may be selected from the list consisting of: noble gases; $H_2$; $O_2$; $N_2$; $CO_2$; Xe; and $SF_6$.

The step of measuring the ion mobilities of the analyte ion through the three different drift gases may comprise: providing each of the different gases in a different drift region; maintaining an electric field along each drift region; pulsing the analyte ion into each drift region; and detecting the drift time of the analyte ion through each drift region.

The method may comprise pulsing the analyte ion into the three different drift regions simultaneously.

The ions may be pulsed into the drift regions simultaneously using the same voltage pulse source.

The step of measuring the ion mobilities of the analyte ion through the different drift gases may comprise: (i) providing a drift region; (ii) maintaining an electric field along the drift region; (iii) pulsing the analyte ion into the drift region; (iv) detecting the drift time of the analyte ion through the drift region; (v) changing the type of gas or gas composition in the drift region to a second gas or gas composition; and (vi) repeating steps (iii) and (iv); and optionally further comprising: (vii) changing the type of gas or gas composition in the drift region to a third gas or gas composition; and (viii) repeating steps (iii) and (iv).

The method may further comprise identifying the analyte ion from the ion mass or a combination of the ion mass and one or more of the ion mobility measurements.

The method may comprise calibrating the mass spectrometer by subjecting one or more type of analyte ion of known mass to the method.

The above described methods may be performed on reference ions so as to calibrate or control the spectrometer during environmental changes, such as to compensate for pressure and/or temperature and/or voltage variations, thereby enabling mass measurements with improved accuracy.

It is contemplated that the simultaneous equations may be solved so as to determine properties of the analyte ion in addition to mass, such as ion radius r and polarizability coefficient φ. Such properties other than or in addition to mass and mobility may be used to filter a library, for example, when searching and/or comparing with theoretical values. For example, these properties may be used when searching and/or filtering data in a database in order to identify the analyte ion.

As the method of separation of the spectrometer is that of ion mobility the separation power of the instrument in the ideal case may be the same as that of a mobility spectrometer, i.e. typically 50-100Ω/δΩ on in terms of cross-section.

The step of measuring the ion mobilities may comprise measuring the ion mobilities of the same type of analyte ion through three different drift gases; and the relationship may be a first equation, wherein said first equation has been derived by, or said method comprises deriving said first equation by: (a) providing separate equations for the ion mobility ($K_n$) of the analyte ion through each of said three different gases in which the ion mobility ($K_n$) is proportional to the collisional cross-section ($\Omega_n$) of the analyte ion in each drift gas (n); (b) providing a separate equation for the collisional cross-section ($\Omega_n$) of the analyte ion in each of said three different gases in which the collisional cross-section is a function of at least one parameter relating to a property of the drift gas, and is a function of at least two parameters relating to properties of the analyte ion; (c) substituting the term for the collisional cross-section ($\Omega_n$) from step (b) for each of the three different drift gases into its corresponding ion mobility equation from step (a), thereby providing three simultaneous equations for the three different gases in which the collisional cross-section variable ($\Omega_n$) is eliminated; and (d) solving or combining the three simultaneous equations so as to eliminate the at least two parameters relating to properties of the analyte ion, and so as to provide said first equation; and (e) determining the mass of the analyte ion by introducing the measured values of the ion mobilities and introducing the values of parameters relating to properties of the drift gases into said first equation such that the mass of the analyte ion is the only unknown variable, and solving the first equation for the mass of the analyte ion.

From a third aspect the present invention provides a method of mass spectrometry comprising:

measuring the ion mobilities of the same type of analyte ion through three different drift gases; and using the measured ion mobilities to determine the mass of the analyte ion from a first equation, wherein said first equation has been derived by, or said method comprises deriving said first equation by:

(a) providing separate equations for the ion mobility ($K_n$) of the analyte ion through each of said three different gases in which the ion mobility ($K_n$) is proportional to the collisional cross-section ($\Omega_n$) of the analyte ion in each drift gas (n);

(b) providing a separate equation for the collisional cross-section ($\Omega_n$) of the analyte ion in each of said three different gases in which the collisional cross-section is a function of at least one parameter relating to a property of the drift gas, and is a function of at least two parameters relating to properties of the analyte ion;

(c) substituting the term for the collisional cross-section ($\Omega_n$) from step (b) for each of the three different drift gases into its corresponding ion mobility equation from step (a), thereby providing three simultaneous equations for the three different gases in which the collisional cross-section variable ($\Omega_n$) is eliminated; and (d) solving or combining the three simultaneous equations so as to eliminate the at least two parameters relating to properties of the analyte ion, and so as to provide said first equation; and (e) determining the mass of the analyte ion by introducing the measured values of the ion mobilities and introducing the values of parameters relating to properties of the drift gases into said first equation such that the mass of the analyte ion is the only unknown variable, and solving the first equation for the mass of the analyte ion.

The analyte ion may be an unknown analyte ion.

One, two or three of said drift gases may be maintained substantially at atmospheric pressure; or one, two or three of said drift gases may be maintained at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) >100 mbar; (viii) >1000 mbar; (ix) 0.0001-0.001 mbar; (x) 0.001-0.01 mbar; (xi) 0.01-0.1 mbar; (xii) 0.1-1 mbar; (xiii) 1-10 mbar; (xiv) 10-100 mbar; and (xv) 100-1000 mbar.

The step of measuring the ion mobilities of the analyte ion through the three different drift gases may comprise measuring the drift time of the analyte ion through each of said three different drift gases.

The ion mobility through any one of the gases may be determined as the length of drift gas that the ion is urged through, divided by the product of the drift time along said length and the electric field strength of the electric field maintained along said length.

Alternatively, the step of measuring the ion mobilities of the analyte ion through the three different drift gases may comprise making measurements of drift time at several voltages and measuring the gradient of a best fit straight line relating inverse voltage to drift time.

The analyte ion may be an ion of a peptide or a small drug molecule.

The three different gases may be selected from the list consisting of: noble gases; $H_2$; $O_2$; $N_2$; $CO_2$; Xe; and $SF_6$.

The step of measuring the ion mobilities of the analyte ion through the three different drift gases may comprise: providing each of the different gases in a different drift region; maintaining an electric field along each drift region; pulsing the analyte ion into each drift region; and detecting the drift time of the analyte ion through each drift region. Alternatively, measurements of drift time may be made at several voltages, and the gradient of a best fit straight line relating inverse voltage to drift time determined.

The method may comprise pulsing the analyte ion into the three different drift regions simultaneously.

The ions may be pulsed into the drift regions simultaneously using the same voltage pulse source.

The step of measuring the ion mobilities of the analyte ion through the different drift gases may comprise: (i) providing a drift region; (ii) maintaining an electric field along the drift region; (iii) pulsing the analyte ion into the drift region; (iv) detecting the drift time of the analyte ion through the drift region; (v) changing the type of gas or gas composition in the drift region to a second gas or gas composition; and (vi) repeating steps (iii) and (iv); and may optionally further comprise: (vii) changing the type of gas or gas composition in the drift region to a third gas or gas composition; and (vi) repeating steps (iii) and (iv).

The method may further comprise identifying the analyte ion from the ion mass.

The method may comprise calibrating the mass spectrometer by subjecting one or more types of analyte ion of known mass to the method.

The above described methods may be performed on reference ions so as to calibrate or control the spectrometer during environmental changes, such as to compensate for pressure and/or temperature and/or voltage variations, thereby providing mass measurements with improved accuracy.

The optional features described in relation to any one of the first, second and third aspects of the present invention may be optional features of any one of the first, second or third aspect of the present invention. For example, the optional features described in relation to the second aspect of the invention may be optional features of the first or third aspect of the invention.

The present invention also provides a mass spectrometer arranged and configured to perform any of the methods described herein.

Accordingly, from the first aspect the present invention provides a mass spectrometer comprising:

one or more ion mobility spectrometers for measuring the ion mobilities of an analyte ion through first, second and third different drift gases;

a memory for storing an algorithm or relationship that relates the ion mobilities of an analyte ion through three gases of different polarizability to the mass of the analyte ion;

a processor having access to said memory; and a controller configured to:

control said one or more ion mobility spectrometers so as to measure the ion mobilities of an analyte ion through first, second and third different drift gases; and control said processor so as to use the measured ion mobilities and said algorithm or relationship to determine the mass of the analyte ion.

From the second aspect the present invention provides a mass spectrometer comprising:

one or more ion mobility spectrometers for measuring the ion mobilities of the same type of analyte ion through three different drift gases (a, b, c); and a processor configured to use the measured ion mobilities to determine the mass of the analyte ion from the following first equation:

$$P_{ab}R_{bc} - P_{bc}R_{ab} + P_{ab}g_c^{1/2}\mu_c^{-1/4} + P_{bc}g_a^{1/2}\mu_a^{-1/4} + P_{ca}g_b^{1/2}\mu_b^{-1/4} = 0$$

wherein for any pair 'i' and 'j' of said drift gases, $P_{ij}$ is the polarizability of drift gas 'i' minus the polarizability of drift gas 'j';

wherein for any pair 'i' and 'j' of said drift gases, $R_{ij}$ is the radius of a drift gas molecule or atom for drift gas 'i' minus the radius of a drift gas molecule or atom for drift gas j;

wherein for any given one of the drift gases n, the quantity $$g_n = \frac{3q}{16 N_n K_n} \sqrt{\frac{2}{\pi k T_n}},$$

where q is the charge of the analyte ion, $N_n$ is the number density of the drift gas n, $K_n$ is the ion mobility of the analyte ion through drift gas n, k is the Boltzmann constant, and $T_n$ is the temperature of drift gas n; and wherein for any given one of the drift gases n, the reduced mass $$\mu_n = \frac{M_n m}{M_n + m},$$

where $M_n$ is the mass of a drift gas molecule or atom for drift gas n, and m is the required mass of the analyte ion.

The spectrometer may have input means for introducing values of the polarizabilities of the drift gases, the radii of the molecules or atoms of the drift gases, $N_n$, $T_n$ and $M_n$ into the first equation.

The spectrometer may be configured to determine the charge q of the analyte ion or have input means for introducing the value of q. Alternatively, the value of q may be assumed to have a fixed value (e.g. one), or masses may be provided for a range of possible charge states.

The processor may be programmed or configured to solve the first equation for the mass of the analyte ion.

From the third aspect the present invention provides a mass spectrometer comprising:

one or more ion mobility spectrometers for measuring the ion mobilities of the same type of analyte ion through three different drift gases; and a processor configured to use the measured ion mobilities to determine the mass of the analyte ion from a first equation, wherein said first equation has been derived by, or said processor is programmed or configured to derive said first equation by:

(a) providing separate equations for the ion mobility ($K_n$) of the analyte ion through each of said three different gases in which the ion mobility ($K_n$) is proportional to the inverse of the collisional cross-section ($\Omega_n$) of the analyte ion in each drift gas (n);

(b) providing a separate equation for the collisional cross-section ($\Omega_n$) of the analyte ion in each of said three different gases in which the collisional cross-section is a function of at least one parameter relating to a property of the drift gas, and is a function of at least two parameters relating to properties of the analyte ion;

(c) substituting the term for the collisional cross-section ($\Omega_n$) from step (b) for each of the three different drift gases into its corresponding ion mobility equation from step (a), thereby providing three simultaneous equations for the three different gases in which the collisional cross-section variable ($\Omega_n$) is eliminated; and (d) solving or combining the three simultaneous equations so as to eliminate the at least two parameters relating to properties of the analyte ion, and so as to provide said first equation; and wherein said processor is configured to determine the mass of the analyte ion by introducing the measured values of the ion mobilities and introducing the values of parameters relating to properties of the drift gases into said first equation such that the mass of the analyte ion is the only unknown variable, and solve the first equation for the mass of the analyte ion.

The spectrometer described herein may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may comprise a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is may be maintained at a pressure selected from the group consisting of: (i) <0.0001 mbar; (ii) 0.0001-

0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

Embodiments of the invention may provide an ambient pressure device based on three parallel low-field ion mobility spectrometers utilising different drift gases and that are used in combination to measure the mass of an analyte ion

BRIEF DESCRIPTION OF THE DRAWINGS

Various embodiments of the present invention will now be described, by way of example only, and with reference to the accompanying drawings in which.

DETAILED DESCRIPTION

Figure 1:
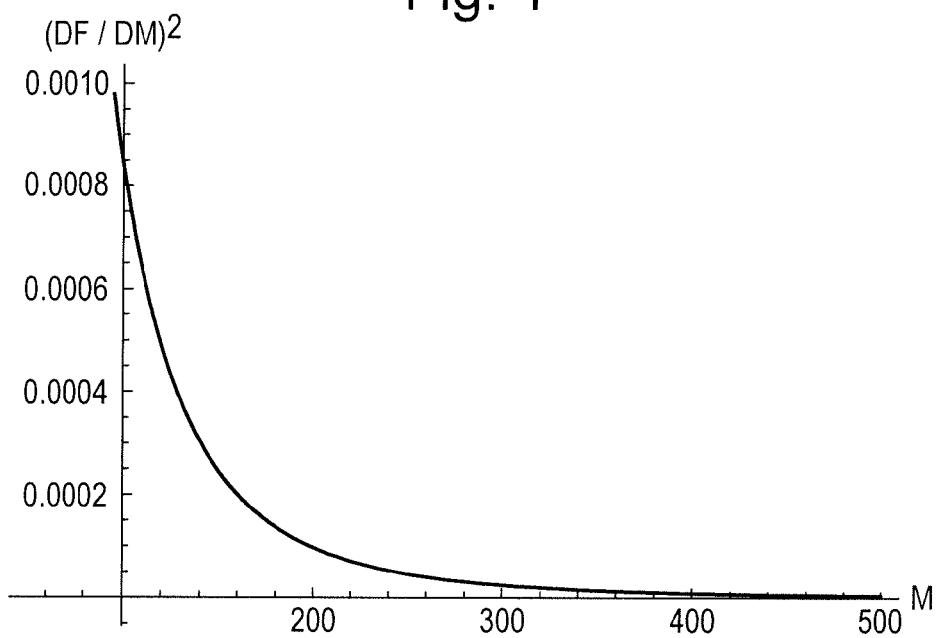
FIG. 1 shows how the precision of the mass measurement of an embodiment of the present invention varies as a function of analyte mass.

Embodiments of the present invention determine the mass of an analyte ion by measuring the ion mobility of the ion through three different gases.

Low electric field ion mobility spectrometry operates on the principle that the velocity of an ion moving through a drift gas is proportional to the electric field applied across the drift gas, with the coefficient of proportionality K being the ion mobility of the ion. Considering a drift gas 'a', then the relationship between the mobility of an ion through that gas ($K_a$) and the collision cross-section of the ion ($\Omega_a$) is given by the Mason-Schamp equation. This defines the ion mobility $K_a$ in terms of the drift gas properties and the mass, charge and collisional cross-section of the ion. The ion mobility $K_a$ is given by:

$$K_a = \frac{3}{16}\sqrt{\frac{2\pi}{\mu_a kT}}\frac{q}{N\Omega_a} \quad (1)$$

where N is the drift gas number density, T is the drift gas temperature, q is the charge of the ion, k is the Boltzman constant, and $\mu_a$ is the reduced mass of the ion and drift gas molecule. The reduced mass of the ion and drift gas molecule $\mu_a$ is given by:

$$\mu_a = \frac{M_a m}{M_a + m} \quad (2)$$

where $M_a$ is the mass of a drift gas atom or molecule, and m is the mass of the analyte ion.

The ion mobility $K_a$ of an ion in drift gas 'a' can be determined by directly measuring the drift time $t_a$ of the ion through a length L of the gas whilst an electric field E is applied across the length L. The ion mobility can then be determined from the well-known equation:

$$K_a = \frac{L}{t_a E} \quad (3)$$

Alternatively, the ion mobility may be determined by making measurements of drift time at several voltages (and therefore electric field strengths) and measuring the gradient of a best fit straight line that relates inverse voltage to drift time. For more details see, for example, Mason, E. A.; McDaniel, E. W. *Transport Properties of Ions in Gases*; Wiley: New York, 1988.

It would be desirable to be able to determine the mass of the analyte ion from the ion mobility value. However, it will be apparent from equations 1 and 2 above that even if the properties of the drift gas are well known, the mass of the analyte ion cannot be determined without prior knowledge of the analyte ion, i.e. without knowing the collision cross-section of the ion ($\Omega_a$).

Beegle et. al. (*International Journal of Mass Spectrometry* 216 (2002), 257-268, "*Effects of drift-gas polarizability on glycine peptides in ion mobility spectrometry*") demonstrated that for a range of compounds, including a number of small peptides and drug standards, the collision cross-section can be parameterised by a radius and polarizability coefficient that depend on the unknown geometric and electronic properties of the analyte ion as well as the polarizability of the gas. In particular, it has been shown by Beegle et al. that the collision cross section depends upon an effective radius of the drift gas ($R_a$) molecule or atom, an effective radius of the ion (r), the polarizability of the drift gas ($P_a$), and an analyte dependent polarizability coefficient ($\varphi$) and is of the form:

$$\Omega_a = \pi(R_a + r + \Phi P_a)^2 \quad (4)$$

Although equation 4 above includes parameters relating to the analyte ion, the inventors have recognised that the relationship may be used in determining the mass of an analyte ion from ion mobility measurements of the analyte ion, without prior knowledge of any properties of the analyte ion. The inventors have recognised that the mass of an analyte can be determined from ion mobility measurements of the analyte ion in three different gases (gases a, b, c). Equations corresponding to equations 1-4 above also apply for each of gases b and c.

Three equations for the collision cross-section in the three drift gases ($\Omega_a$, $\Omega_b$, $\Omega_c$) can be derived from equation (1) above. The values of ion mobility in each gas ($K_a$, $K_b$, $K_c$) can be experimentally determined without prior knowledge of the analyte ion, as described above in relation to equation 3.

The collisional cross-section ($\Omega_a$) for drift gas 'a' is given by equation 4 above. Corresponding equations apply for the collisional cross-section ($\Omega_b$) of the analyte ion in drift gas 'b' and the collisional cross-section ($\Omega_s$) of the analyte ion in drift gas 'c'. Substituting the expressions for ($\Omega_a$, $\Omega_b$, $\Omega_c$) corresponding to equation 4 into the expressions for ($\Omega_a$, $\Omega_b$, $\Omega_c$) derived from equation 1 yields three simultaneous equations.

The properties of the drift gases (a,b,c) are known and hence the polarizability of each drift gas is known. Polarizabilities for most commonly available gases are available in standard references, e.g. the CRC Handbook of Chemistry and Physics. As such, the three simultaneous equations include three unknowns, each unknown relating to the analyte. The three unknowns are the analyte radius r, the polarizability coefficient $\varphi$ and the analyte mass m. Solving the simultaneous equations so as to eliminate r and $\varphi$ yields an implicit equation for the unknown mass, m of the analyte ion, which depends only on known parameters. This equation is as follows:

$$P_{ab}R_{bc} - P_{bc}R_{ab} + P_{ab}g_c^{1/2}\mu_c^{-1/4} + P_{bc}g_a^{1/2}\mu_a^{-1/4} + P_{ca}g_b^{1/2} \\ 2\mu_b^{-1/4} = 0 \quad (5)$$

where $P_{ij}=P_i-P_j$ and $R_{ij}=R_i-R_j$ for any pair of gases 'i' and 'j', and where:

$$g_a = \frac{3q}{16NK_a}\sqrt{\frac{2}{\pi kT}} \quad (6)$$

$$g_b = \frac{3q}{16NK_b}\sqrt{\frac{2}{\pi kT}} \quad (7)$$

$$g_c = \frac{3q}{16NK_c}\sqrt{\frac{2}{\pi kT}} \quad (8)$$

The mass of the analyte m is present in the reduced mass terms ($\mu_a,\mu_b,\mu_c$) in equation 5 above (also see equation 2 above). Each of the reduced mass terms is raised to the power of minus ¼. This weak dependence means that mass is not well constrained, in general, and that it is preferred to choose drift gases that maximise the resolution of the instrument over a desired analyte mass range. It is generally beneficial to choose gases with as wide a range of polarizabilties as possible. It is also necessary to chooses drift gases that exhibit, at least approximately, the relationship described by equation 4 above for the analyte or analytes of interest. This may be tested empirically by performing the method of the invention using analyte ions having known masses and determining if the experimentally determined masses match the known masses.

An analytic solution to equation 5 above is possible for the limit in which the masses of the drift gas molecules ($M_a,M_b,M_c$) are much less than the mass of the analyte, but a numerical solution may be obtained straightforwardly in all cases.

The sensitivity of the analyser to various perturbations over a given analyte mass range has been explored numerically for a variety of combinations of different drift gases, including the noble gases, $H_2$, $O_2$, $N_2$, and $CO_2$. It was found that the combination of the three different drift gases being $H_2$, Xe and $SF_6$ was in some sense optimal over the analyte mass range of 50 to 500 Da. For mass measurements of the polyglycine peptides G1 to G6, the combination Kr, Xe, $CO_2$ was found to be optimal with respect to small deviations from a linear relationship between polarizability and analyte radius.

FIG. 1 shows how the square of the derivative of the solution of equation 5 with respect to analyte mass varies as a function of analyte mass when the three different drift gases are $H_2$, Xe and $SF_6$. This shows that when the absolute value of this gradient is high, the solution is more tolerant to measurement uncertainties, and mass measurement is therefore more precise.

Figure 2:
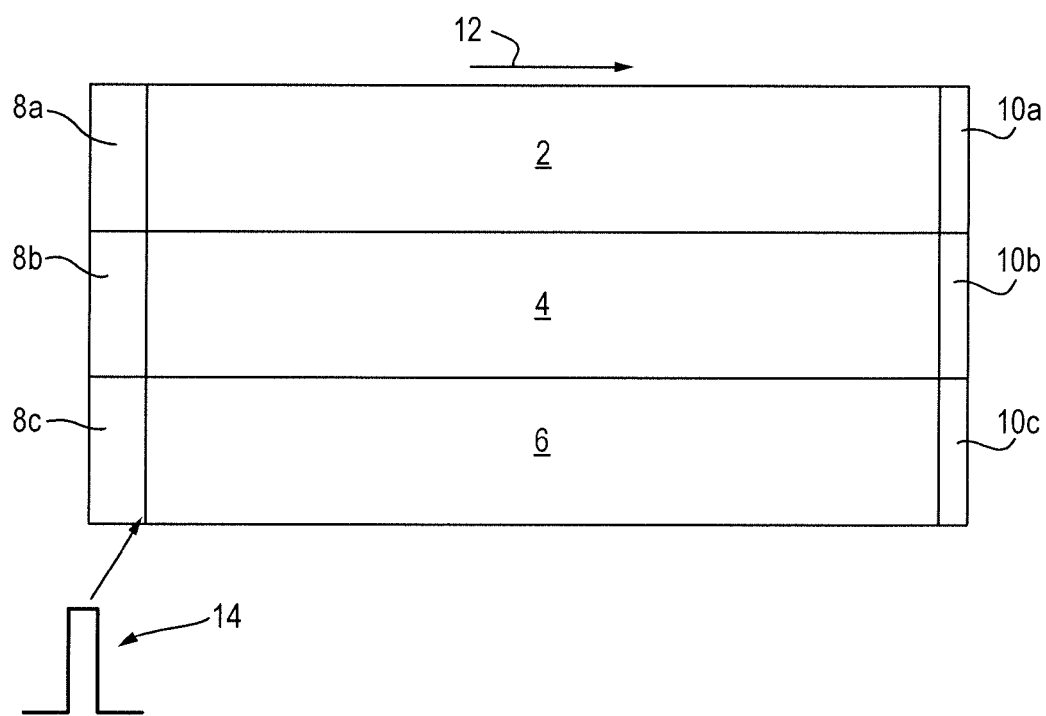
FIG. 2 shows a schematic of an embodiment of the analyser.

FIG. 2 shows a schematic of the analyser for performing the above method. The analyser comprises three different drift tubes 2,4,6 that are filled with the different drift gases $H_2$, Xe and $SF_6$. An ion introduction port 8a-8c is provided at one end of each drift tube 2,4,6 for introducing the analyte sample ions into the drift tube 2,4,6. An ion detector 10a-10c is provided at the other end of each drift tube 2,4,6 for detecting the analyte ions. An electric field 12 is maintained along each drift tube 2,4,6 so as to drive the analyte ions through the drift tube 2,4,6.

In operation, analyte ions are pulsed into each of the three different drift tubes 2,4,6 by a gate pulse 14. The ions are then driven through the drift gas in each drift tube 2,4,6 by the electric field 12 that is maintained along the drift tube 2,4,6. The ions are then detected at the exit of each drift tube 2,4,6 by the detector 10a-10c so as to determine the duration of time taken for the analyte ions to pass through each drift tube 2,4,6. The same type of analyte ion takes different times to pass through the different drift tubes 2,4,6, as the drift tubes 2,4,6 contain different drift gases. The ion mobilities of the same analyte ion in the different gases are then determined according to equation 3 above. Alternatively, as mentioned above, the ion mobilities may be determined by making a range of drift time measurements at different drift tube voltages. As the properties of the drift gases are known, equation 5 above may then be used to determine the mass of the analyte ion.

The analyser in FIG. 2 may have a common power supply for simultaneously pulsing ions into the different drift tubes 2,4,6. The drift tubes 2,4,6 may be mechanically integrated so as to minimize cost.

Although the present invention has been described with reference to various embodiments, it will be understood by those skilled in the art that various changes in form and detail may be made without departing from the scope of the invention as set forth in the accompanying claims.

For example, it has been assumed for simplicity that the pressure and temperature, and therefore the number density N, of each drift gas is the same. However, it is contemplated herein that the temperatures and/or pressures of the different drift gases may be different.

Although the drift length L through the different drift gases and the electric field strength E across the different drift gases have been assumed to be the same, it is contemplated that the drift length and/or electric field strength may be different in the different gases.

Although embodiments have been described that include three drift tubes that contain different drift gases, it is contemplated that only one or two drift tubes may be employed and that the gas composition in said one or two tubes may be changed with time so as to provide the three different gas compositions necessary. It is also contemplated that more than three different drift gas compositions may be provides for additional specificity. For example, at least four drift tubes containing different drift gases may be used.

Methods of calculating the mass of the analyte ion from the ion mobilities are contemplated other than by using equation 5 above. For example, rather than using equation 5 to directly calculate the mass using the known conditions, it is possible to use a calibration approach. To give one example, equation 5 can be written in the form:

$$\alpha + \frac{\beta_a}{\mu_a^{1/4}\sqrt{K_a}} + \frac{\beta_b}{\mu_b^{1/4}\sqrt{K_b}} + \frac{\beta_c}{\mu_c^{1/4}\sqrt{K_c}} \quad (9)$$

As long as the masses of the gas molecules or atoms $M_a$, $M_b$ and $M_c$ are known, then $\alpha$, $\beta_a$, $\beta_b$, and $\beta_c$ may be treated as unknown parameters to be calibrated using mass standards. In this case at least four mass standards would be required, although more than four mass standards could be used if available.

In a semi-empirical approach various correction terms could be added to equation (9) to absorb deviations from the pure Beegle relationship (equation 4) and/or imperfections in the apparatus and so forth.

In a fully empirical approach, any sufficiently flexible parameterised function F satisfying $$F(K_a,K_b,K_c,m,\alpha_1,\alpha_2,\ldots)=0 \quad (10)$$

may be defined. In this equation $K_a$, $K_b$ and $K_c$ are the three mobility measurements, m is the analyte mass and $\alpha_1$, $\alpha_2$ . . . $\alpha_n$ are n calibration parameters to be determined. When these parameters have been determined, equation (10) may be solved either analytically or numerically for mass m given three mobility measurements.

In a completely empirical approach, the explicit function F can be replaced by a machine learning algorithm that is trained to calculate mass using a sufficiently large calibration dataset.

The empirical approaches to mass measurement described above generalise straightforwardly to devices with more than three gases, or more than three drift tubes.

Although drift tube ion mobility spectrometers have been described above in which ions are driven through the gas by a static potential gradient, it is alternatively contemplated that ions may be driven through the gas by one or more potential barriers or wells that travel along the drift region. Alternatively, it is contemplated that the ions may be separated by high-field asymmetric waveform ion mobility spectrometry (FAIMS), rather than the drift ion mobility separation described above.

The invention claimed is:

1. A method of mass spectrometry comprising:
   measuring the ion mobilities of an analyte ion through first, second and third different drift gases of different polarizability; and
   providing an algorithm or relationship that relates the ion mobilities of the analyte ion through the three gases of different polarizability to the mass of the analyte ion; and
   using the measured ion mobilities and said algorithm or relationship to determine the mass of the analyte ion.

2. The method of claim 1, wherein the only variables in the algorithm or relationship other than said mass are variables representative of the ion mobilities of the analyte ion through the three different drift gases; or
   wherein the only variables in the algorithm or relationship other than said mass are variables representative of the ion mobilities of the analyte ion through the three different drift gases and physicochemical properties of the three different drift gases; and the method comprises using the measured ion mobilities, said physicochemical properties of the first, second and third drift gases, and said algorithm or relationship to determine the mass of the analyte ion.

3. The method of claim 1, further comprising measuring the ion mobilities through said three gases of at least four different mass standard ions of known mass, and using these measured ion mobilities and known masses to derive said algorithm or relationship.

4. A method of mass spectrometry comprising:
   measuring the ion mobilities of the same type of analyte ion through three different drift gases (a, b, c); and
   using the measured ion mobilities to determine the mass of the analyte ion from the following first equation:

$$P_{ab}R_{bc} - P_{bc}R_{ab} + P_{ab}g_c^{1/2}\mu_c^{-1/4} + P_{bc}g_a^{1/2}\mu_a^{-1/4} P_{ca}g_b^{1/2} 2\mu_b^{-1/4} = 0$$

wherein for any pair 'i' and 'j' of said drift gases, $P_{ij}$ is the polarizability of drift gas 'i' minus the polarizability of drift gas 'j';
wherein for any pair 'i' and 'j' of said drift gases, $R_{ij}$ is the radius of a drift gas molecule or atom for drift gas i minus the radius of a drift gas molecule or atom for drift gas j;
wherein for any given one of the drift gases n, the quantity $$g_n = \frac{3q}{16 N_n K_n} \sqrt{\frac{2}{\pi k T_n}},$$

where q is the charge of the analyte ion, $N_n$ is the number density of the drift gas n, $K_n$ is the ion mobility of the analyte ion through drift gas n, k is the Boltzmann constant, and $T_n$ is the temperature of drift gas n; and
wherein for any given one of the drift gases n, the reduced mass $$\mu_n = \frac{M_n m}{M_n + m},$$

where $M_n$ is the mass of a drift gas molecule or atom for drift gas n, and m is the required mass of the analyte ion.

5. The method of claim 4, comprising determining the mass of the analyte ion by introducing the measured values of the ion mobilities ($K_n$) into the first equation; introducing known values, or measuring and introducing values, of $P_{ij}$, $R_{ij}$, q, $N_n$, $T_n$ and $M_n$ into the first equation; and solving the first equation for the mass of the analyte ion.

6. The method of claim 1, wherein said step of measuring the ion mobilities of the analyte ion through the different drift gases comprises measuring the drift time of the analyte ion through each of the three different drift gases.

7. The method of claim 1, wherein said relationship or first equation is derived by, or said method comprises deriving said relationship or first equation by:
   (a) providing an equation for the ion mobility $K_n$ of the analyte ion through each of the three different gases, the equation being of the form:

$$K_n = \frac{3q}{16 N_n \Omega_n} \sqrt{\frac{2}{\mu_n k T_n}},$$

where $\Omega_n$ is the collisional cross-section of the analyte ion in a given drift gas (n);
   (b) providing an equation for the collisional cross-section of the analyte ion in each of the three different gases, the equation being of the form: $\Omega_n = \pi(R_n + r + \Phi P_n)^2$, where $R_n$ is the radius of a drift gas molecule or atom in a given drift gas (n), r is the radius of the analyte ion, $\varphi$ is the polarizability coefficient, and $P_n$ is the polarizability of a given drift gas (n);
   (c) substituting the term for the collisional cross-section from step (b) for each of the three different drift gases into its corresponding ion mobility equation from step (a), thereby providing three simultaneous equations for the three different gases in which the variable $\Omega_n$ is eliminated; and
   (d) solving or combining the three simultaneous equations so as to eliminate $\varphi$ and r, and so as to provide said first equation.

8. The method of claim 1, wherein each of the drift gases exhibits the relationship $\Omega_n = \pi(R_n + r + \Phi P_n)^2$, where $R_n$ is the radius of a drift gas molecule or atom in a given drift gas (n), r is the radius of the analyte ion, $\varphi$ is the polarizability coefficient, and $P_n$ is the polarizability of a given drift gas (n).

9. The method of claim 1, wherein the three different drift gases are selected from the list consisting of: noble gases; $H_2$; $O_2$; $N_2$; $CO_2$; Xe; and $SF_6$.

10. The method of claim 1, wherein the step of measuring the ion mobilities of the analyte ion through the three different drift gases comprises:
providing each of the different gases in a different drift region;
maintaining an electric field along each drift region;
pulsing the analyte ion into each drift region; and
detecting the drift time of the analyte ion through each drift region.

11. The method of claim 10, comprising pulsing the analyte ion into the three different drift regions simultaneously.

12. The method of claim 1, wherein the step of measuring the ion mobilities of the analyte ion through the different drift gases comprises:
(i) providing a drift region;
(ii) maintaining an electric field along the drift region;
(iii) pulsing the analyte ion into the drift region;
(iv) detecting the drift time of the analyte ion through the drift region;
(v) changing the type of gas or gas composition in the drift region to a second gas or gas composition; and
(vi) repeating steps (iii) and (iv); and optionally further comprising:
(vii) changing the type of gas or gas composition in the drift region to a third gas or gas composition; and
(viii) repeating steps (iii) and (iv).

13. The method of claim 1, further comprising identifying the analyte ion from the ion mass.

14. A method of mass spectrometry comprising:
measuring the ion mobilities of the same type of analyte ion through three different drift gases; and
using the measured ion mobilities to determine the mass of the analyte ion from a first equation, wherein said first equation has been derived by, or said method comprises deriving said first equation by:
(a) providing separate equations for the ion mobility ($K_n$) of the analyte ion through each of said three different gases in which the ion mobility ($K_n$) is proportional to the collisional cross-section ($\Omega_n$) of the analyte ion in each drift gas (n);
(b) providing a separate equation for the collisional cross-section ($\Omega_n$) of the analyte ion in each of said three different gases in which the collisional cross-section is a function of at least one parameter relating to a property of the drift gas, and is a function of at least two parameters relating to properties of the analyte ion;
(c) substituting the term for the collisional cross-section ($\Omega_n$) from step (b) for each of the three different drift gases into its corresponding ion mobility equation from step (a), thereby providing three simultaneous equations for the three different gases in which the collisional cross-section variable ($\Omega_n$) is eliminated; and
(d) solving or combining the three simultaneous equations so as to eliminate the at least two parameters relating to properties of the analyte ion, and so as to provide said first equation; and
(e) determining the mass of the analyte ion by introducing the measured values of the ion mobilities and introducing the values of parameters relating to properties of the drift gases into said first equation such that the mass of the analyte ion is the only unknown variable, and solving the first equation for the mass of the analyte ion.

15. A mass spectrometer arranged and configured to perform the method of claim 1.

16. The method of claim 1, wherein said algorithm or relationship comprises a machine learning algorithm.

17. The method of claim 16, further comprising training said machine learning algorithm using a calibration dataset.

18. A method of mass spectrometry comprising:
measuring the ion mobilities of an analyte ion through first, second and third different drift gases; and
using the measured ion mobilities in an algorithm or relationship to determine the mass of the analyte ion.

* * * * *